(12) United States Patent  (10) Patent No.: US 8,187,758 B2
Fisher et al.  (45) Date of Patent: May 29, 2012

(54) FUEL CELL APPARATUS WITH A SPLIT PUMP

(75) Inventors: Tobin Joseph Fisher, San Francisco, CA (US); Jonathan Louis Glassman, Indianapolis, IN (US)

(73) Assignee: Ardica Technologies Inc., San Francisco, CA (US)

( * ) Notice: Subject to any disclaimer, the term of this patent is extended or adjusted under 35 U.S.C. 154(b) by 1348 days.

(21) Appl. No.: 11/203,001

(22) Filed: Aug. 11, 2005

(65) Prior Publication Data

US 2007/0037034 A1  Feb. 15, 2007

(51) Int. Cl.
*H01M 8/06* (2006.01)
*F04B 7/00* (2006.01)

(52) U.S. Cl. ........ 429/421; 429/416; 429/515; 429/512; 417/510

(58) Field of Classification Search .................... 429/34, 429/38, 25, 22, 19; 417/510; 220/582, 500, 220/553; 137/803, 804, 814; 222/61, 94
See application file for complete search history.

(56) References Cited

U.S. PATENT DOCUMENTS

| | | | |
|---|---|---|---|
| 3,774,589 A | 11/1973 | Kober | |
| 4,846,176 A | 7/1989 | Golden | |
| 5,817,157 A | 10/1998 | Checketts | |
| 6,250,078 B1 | 6/2001 | Amendola | |
| 6,326,097 B1 | 12/2001 | Hockaday | |
| 6,375,638 B2 | 4/2002 | Nason | |
| 6,392,313 B1 | 5/2002 | Epstein | |
| 6,433,129 B1 | 8/2002 | Amendola | |
| 6,468,694 B1 | 10/2002 | Amendola | |
| 6,497,973 B1 | 12/2002 | Amendola | |
| 6,524,542 B2 | 2/2003 | Amendola | |
| 6,534,033 B1 | 3/2003 | Amendola | |
| 6,544,400 B2 | 4/2003 | Hockaday | |
| 6,544,679 B1 | 4/2003 | Petillo | |
| 6,579,068 B2 | 6/2003 | Bridger | |
| 6,586,563 B1 | 7/2003 | Ortega | |
| 6,645,651 B2 | 11/2003 | Hockaday | |
| 6,660,685 B1 | 12/2003 | Schussler | |
| 6,670,444 B2 | 12/2003 | Amendola | |
| 6,683,025 B2 | 1/2004 | Amendola | |
| 6,706,909 B1 | 3/2004 | Snover | |
| 6,713,201 B2 | 3/2004 | Bullock | |
| 6,723,072 B2 | 4/2004 | Flaherty | |
| 6,745,801 B1 | 6/2004 | Cohen | |
| 6,808,833 B2 | 10/2004 | Johnson | |
| 6,818,334 B2 | 11/2004 | Tsang | |

(Continued)

FOREIGN PATENT DOCUMENTS

DE  4221492  *  6/1992

(Continued)

*Primary Examiner* — Raymond Alejandro
(74) *Attorney, Agent, or Firm* — Jeffrey Schox (57) ABSTRACT

A fluid pump and connector assembly is particularly suited for use in connecting a fuel cartridge to a fuel cell system. The assembly has a first sub-assembly comprising a fluid inlet, a fluid outlet, a flexible diaphragm in fluid communication with the inlet and outlet, and a first connector. The assembly also has a second sub-assembly comprising a second connector adapted to connect to the first connector, an actuator and a reciprocating member coupled to the actuator and contacting the diaphragm when the first and second sub-assemblies are connected, wherein a reciprocating motion of the actuator and member causes the diaphragm to reciprocate and pump fluid from the inlet to the outlet without exposing the fluid to the second sub-assembly.

12 Claims, 6 Drawing Sheets

U.S. PATENT DOCUMENTS

| | | |
|---|---|---|
| 6,821,499 B2 | 11/2004 | Jorgensen |
| 6,834,623 B2 | 12/2004 | Cheng |
| 6,834,632 B2 | 12/2004 | Kataoka |
| 6,840,955 B2 | 1/2005 | Ein |
| 6,849,351 B2 | 2/2005 | Hartnack |
| 6,887,596 B2 | 5/2005 | Leban |
| 6,916,159 B2 | 7/2005 | Rush |
| 6,924,054 B2 | 8/2005 | Prasad |
| 7,105,033 B2 | 9/2006 | Strizki |
| 7,105,245 B2 | 9/2006 | Ohlsen |
| 7,316,719 B2 | 1/2008 | Devos |
| 7,645,536 B2 | 1/2010 | Akiyama |
| 7,666,386 B2 | 2/2010 | Withers-Kirby |
| 2002/0182459 A1* | 12/2002 | Hockaday et al. .............. 429/19 |
| 2003/0009942 A1 | 1/2003 | Amendola |
| 2003/0037487 A1 | 2/2003 | Amendola |
| 2003/0082427 A1 | 5/2003 | Prasad |
| 2003/0138679 A1 | 7/2003 | Prased |
| 2003/0198558 A1 | 10/2003 | Nason |
| 2003/0235724 A1 | 12/2003 | Ord |
| 2004/0011662 A1 | 1/2004 | Xu |
| 2004/0052704 A1 | 3/2004 | Devos |
| 2004/0062965 A1 | 4/2004 | Morse |
| 2004/0062978 A1 | 4/2004 | Yazici |
| 2004/0131903 A1 | 7/2004 | Shioya |
| 2004/0148857 A1 | 8/2004 | Strizki |
| 2004/0197214 A1 | 10/2004 | Arthur |
| 2004/0202548 A1 | 10/2004 | Dai |
| 2004/0211054 A1 | 10/2004 | Morse |
| 2004/0229101 A1 | 11/2004 | Davis |
| 2004/0253500 A1 | 12/2004 | Bourilkov |
| 2005/0037252 A1 | 2/2005 | Pham |
| 2005/0089415 A1 | 4/2005 | Cho |
| 2005/0181250 A1* | 8/2005 | Beckmann et al. .............. 429/24 |
| 2006/0127734 A1 | 6/2006 | McLean |
| 2006/0172694 A1* | 8/2006 | Gau et al. ...................... 454/333 |
| 2006/0196112 A1* | 9/2006 | Berry et al. ...................... 44/550 |
| 2006/0275645 A1 | 12/2006 | Gallagher |
| 2007/0020172 A1 | 1/2007 | Withers-Kirby |
| 2007/0042244 A1 | 2/2007 | Spallone |
| 2007/0166595 A1* | 7/2007 | Akiyama et al. ................ 429/34 |
| 2010/0150824 A1 | 6/2010 | Withers-Kirby |

FOREIGN PATENT DOCUMENTS

| | | | |
|---|---|---|---|
| WO | WO 00/12889 | * | 3/2000 |
| WO | WO 2005/057703 | * | 6/2005 |

* cited by examiner

FUEL CELL APPARATUS WITH A SPLIT PUMP

FIELD OF THE INVENTION

This invention relates generally to a fluid pump and connector assembly, for connecting a fluid container to another device and for pumping fluid in the fluid container.

BACKGROUND OF INVENTION

Modern portable electronic devices are demanding increasing amounts of electrical power and chemical batteries are often the performance bottleneck for such devices. Wireless products, such as personal digital assistants, mobile phones, entertainment devices, and next generation laptops in particular have a great demand for sustained power. For long-term portable operations, fuel cells are an attractive solution. Fuel cells, like batteries, efficiently convert chemical energy into electricity, but have additional advantages, such as higher energy density and the capability for instant refuelling. Fuel cells are typically fuelled by hydrogen gas, but there are technological challenges in storing and delivering hydrogen gas to the fuel cells in a cost effective and efficient manner. One particular challenge is to provide a fuel supply that is inexpensive, safe, light and compact enough to be readily portable yet store enough hydrogen to provide a useful amount of fuel to the fuel cell. State of the art means for storing hydrogen include metal hydride canisters to store hydrogen at relatively low pressures, and pressure tanks to store compressed hydrogen at elevated pressures. Both approaches have drawbacks; for example, metal hydride storage is relatively safe but has a low energy density to weight ratio, and compressed hydrogen storage can have a high energy density to weight ratio but requires high strength and expensive containment solutions.

Research has been conducted into using liquid methanol as a fuel and designing a "direct methanol" fuel cell that electrochemically produces electricity directly from methanol; however, significant technological challenges exist such as preventing methanol cross-over through the electrolyte membrane, and preventing catalyst poisoning by the methanol fuel.

Other efforts have been directed at generating hydrogen gas from a hydrogen-containing fuel solution such as sodium borohydride. In such approaches, the fuel solution is exposed to a catalyst to facilitate the production of hydrogen gas. While this approach is promising, technological challenges exist in containing the caustic fuel solution and preventing leakage, especially when the portable fuel cell system will be used in close proximity to humans.

SUMMARY OF THE INVENTION

It is an object of the invention to provide a means for safely and cost effectively pumping a fluid within a fluid container without removing the fluid from the container.

According to one aspect of the invention, there is provided a fluid pump comprising two interconnectable sub-assemblies. A first sub-assembly comprises a fluid inlet, a fluid outlet, and a flexible diaphragm in fluid communication with the inlet and outlet. A second sub-assembly comprises an actuator and a reciprocating member coupled to the actuator. The reciprocating member contacts the diaphragm when the first and second sub-assemblies are connected. A reciprocating motion of the actuator and member causes the diaphragm to reciprocate and pump fluid from the inlet to the outlet without exposing the fluid to the second sub-assembly.

The sub-assemblies can be provided with magnetic connectors which enable the sub-assemblies to be removably interconnected. The first sub-assembly can be mounted to a fuel cartridge and the fluid can be a liquid reactant that generates hydrogen when mixed with a solid reactant. The liquid reactant can be a citric acid solution and the solid reactant can be sodium borohydride.

The second sub-assembly can be mounted to a fuel cell system and have an intake port for receiving hydrogen gas produced by the fuel cartridge and delivering the hydrogen gas to a fuel cell in the fuel cell system.

The actuator can be a shape memory alloy that is electrically coupled to an electrical source capable of heating the shape memory alloy to above a shrinkage temperature. In particular, the actuator can be a nitinol wire coupled to the reciprocating member and attached at both ends to crimping connectors to form a bow-shaped configuration. The wire can be mounted so that when in a relaxed phase, the reciprocating member is in a retracted position, and when in a contracted phase, the reciprocating member is in an extended position. Pulsing electrical current to the wire will cause the wire to cycle between the relaxed and contracted phases, causing the reciprocating member and diaphragm to reciprocate.

Since the actuator and reciprocating components are located in the second sub-assembly, the manufacturing costs of the first sub-assembly can be reduced, enabling the fuel cartridge to be manufactured at a sufficiently low cost to be a single use disposable product. Furthermore, the first sub-assembly keeps the reactants entirely within the fuel cartridge, which reduces the chances of leakage and consequent harm to a user, or to equipment in close proximity.

DETAILED DESCRIPTION OF EMBODIMENTS OF THE INVENION

Figure 1:
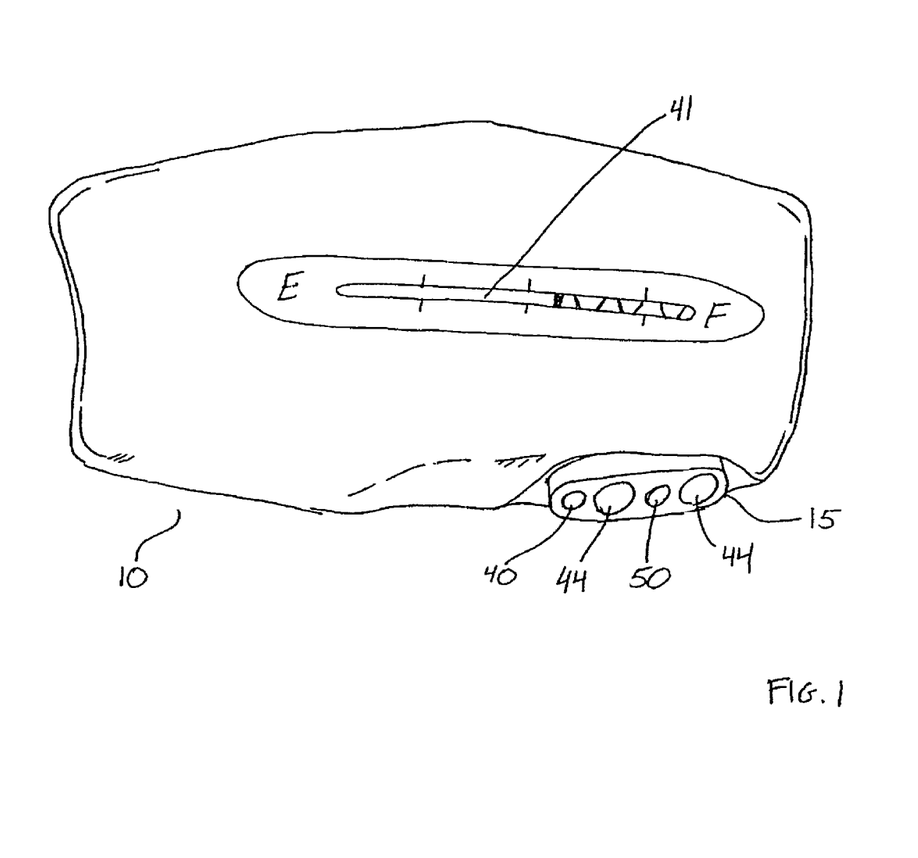
FIG. 1 is a side view of a hydrogen generating fuel cartridge having a fuel cell connector sub-assembly.
Figure 2:
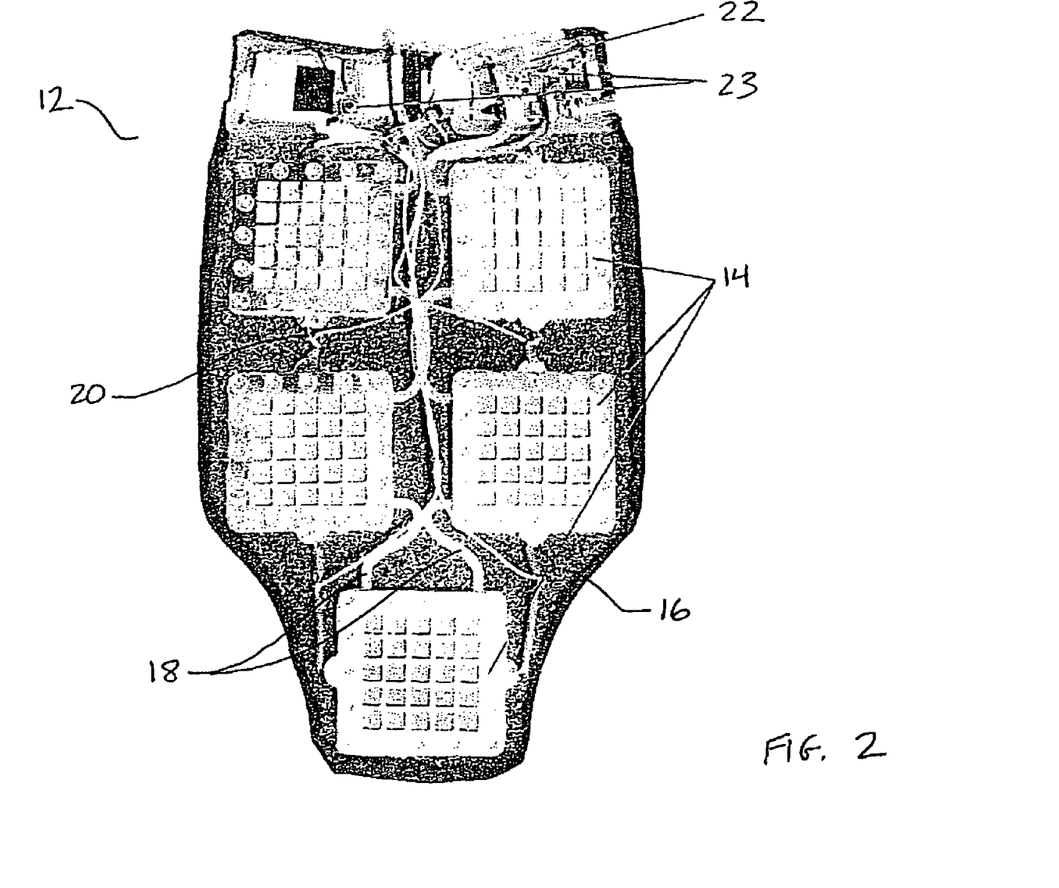
FIG. 2 is a partially disassembled view of a fuel cell system having a planar fuel cell stack, a control module, and a connector and pump sub-assembly for coupling to the fuel cartridge sub-assembly and pumping fluid inside the fuel cartridge.

According to one embodiment of the invention and referring to FIG. 1, a portable fuel cartridge 10 generates hydrogen gas for use as fuel by a fuel cell. Referring to FIG. 2, a portable fuel cell system 12 comprises fuel cells 14 which generate electricity by electrochemically reacting hydrogen gas and oxygen in ambient air. The by-products of the electrochemical reaction also include water and heat. The generated electricity can be used to power portable electrical devices, and to provide heat. The portable fuel cartridge 10 has a connector sub-assembly 15 for physically and fluidly coupling the fuel cell cartridge 10 to the fuel cell system 12. Once coupled, hydrogen gas generated by the fuel cartridge 10 can be delivered into the fuel cell system 12 for use by the fuel cells 14.

One particular use contemplated for the fuel cartridge 10 and fuel cell system 12 is to provide heat and electrical power to personal apparel, such as a jacket. The fuel cell system 12 shown in FIG. 2 is particularly suited for such use. Each fuel cell 14 is arranged in a planar array and electrically connected in series to form a stack. The fuel cells 14 are embedded in a spaced manner within a flexible foam and fabric laminate frame 16. Flexible fuel conduits 18 and electrical conductors 20 interconnect each fuel cell 14. The fuel outlet of one fuel cell 14 is fluidly coupled to the fuel inlet of the adjacent downstream fuel cell 14 by the fuel conduits 18. The fuel cell stack has a dead-ended fuel flow design, in which the last fuel cell 14 is coupled to a purge valve, which can be periodically opened to discharge contaminants and water in the fuel cell stack. The first fuel cell 14 is fluidly coupled to a pumping and connector sub-assembly 22, which is provided with means for fluidly and physically coupling to the connector sub-assembly 15 of the fuel cartridge 10. A control system 23 for controlling the operation of the fuel cell system is electrically communicative with the pumping and connector sub-assembly 22 to control operation of the pump, the purge valve, a voltage sensor and pressure sensor (not shown) coupled to electrical conductors 20, and, a user interface controls and display (not shown).

The fuel cells 14 are planar, passive air breathing proton exchange membrane (PEM) type fuel cells. Each fuel cell comprises a conventional platinum catalyst-coated electrode and NAFION™ membrane electrode assembly (MEA), sandwiched by cathode and anode assemblies (not shown). The cathode assembly comprises a conductive mesh in adjacent contact to the cathode side of the MEA, and a conductive plate with multiple openings there-through in adjacent contact with the conductive mesh; the multiple openings are exposed to air and provide access to oxygen used in the electrochemical reaction. The anode assembly comprises a conductive anode plate with serpentine flow channels in adjacent contact with the anode side of the MEA, and a hydrogen gas manifold plate and having hydrogen inlet and outlet and manifolds that fluidly couple to inlet and outlet ends of the anode plate fuel flow channels. The inlet and outlet manifolds fluidly couple to respective inlet and outlet fuel conduits 18. The MEA also features adhesive around its periphery, and with the adhesive layer, bonds the fuel cell components together.

The fuel cell stack 12 in this embodiment is configured to provide about 10 watts of power; however it is within the scope of the invention to scale up or down the power output by changing the number of fuel cells, or substituting fuel cells of different performance ratings.

Such planar PEM fuel cells 14 are well known in the art and are not described in any further detail here. While the fuel cell system 12 is particularly suited for PEM fuel cells, other fuel cell types that are fuelled by hydrogen gas can be substituted, such as solid oxide fuel cells, phosphoric acid fuel cells and alkaline fuel cells. Also, other known PEM fuel cell designs can be readily substituted.

Because the fuel cells 14 are embedded in the flexible frame 16 and are interconnected by flexible conduits 18 and electrical connectors 20, the shape of fuel cell system 12 can be changed; this feature is particularly advantageous for use in apparel, as the fuel cell system 10 can conform to the shape of the wearer. Preferably, the fuel system 12 is installed along the upper spine region of the jacket, so that the fuel cells 14 in the stack can conform to the shape of the wearer's back. However, it is within the scope of the invention for the fuel cell system 12 to assume different configurations, e.g. a conventional vertically arranged stack. In such alternative configurations, the fuel cells in the stack would not necessarily be flexibly interconnected, and installation of such fuel cell stacks in apparel would be modified to prevent discomfort to the user. Also, while five fuel cells 14 are shown in this embodiment, it is within the scope of the invention to scale up or down the number of fuel cells and the corresponding power output depending on the particular application and power need.

Two layers of soft flexible foam are used to sandwich the gas, current, and voltage sensing interconnects within the fuel cell system. These parts hold the system interconnects in place and provide strain relief against mechanical forces (bending, stretching, etc.) put on the system. Additionally, they provide a lightweight covering for the interconnecting elements (wire, tubes, voltage sensing wires) that hides these parts from the user and creates a soft, body friendly packaging.

In the current embodiment, a wicking type fabric is laminated over the outside of the system covering a plane including the cathodes of the fuel cells 14. This material is designed to rapidly evaporate any moisture in contact with it. Placing this material in contact with the cathode enables a rapid evaporation of any moisture that collects on the cathode of the fuel cell 14, reducing the risk of flooding in the cells 14. Covering the entire system 12 with this fabric maximizes the surface area for evaporation. Additionally, this fabric serves as a flexible strain-relieving interconnect between the multiple fuel cells 14 in the system 12. Lastly, this fabric creates a surface texture for the fuel cell system 12 that feels soft and pleasant when used close to the skin, making the product more comfortable for near-body applications.

Preferably, the fuel cartridge 10 is constructed from lightweight and inexpensive materials to enable the fuel cartridge 10 to be easily portable and disposable after a single use. In this embodiment and as shown schematically in FIG. 3, the fuel cartridge 10 stores a liquid reactant, namely, a 28 wt. % citric acid solution, in an outer bag 25 and a solid reactant, namely, a compacted and fused sodium borohydride ($NaBH_4$) powder, in a tubular reaction chamber 26. The reaction chamber 26 (TEFLON® tubing, 0.60", 0.030" wall, McMaster) is stored within an inner bag 27 that is fluidly sealed from the solution bag 25. The $NaBH_4$ powder is compacted into a cylindrical pill 28, and a spring 29 inside the reaction chamber 26 biases the pill 28 against an outlet having a separator screen 30 at one end of the reaction chamber 26. In the current embodiment, a 0.5" diameter pill was formed by pressing approximately 12 grams of Sodium Borohydride powder under 7 tons of force to form a pill 3.2 inches in length.

Figure 3:
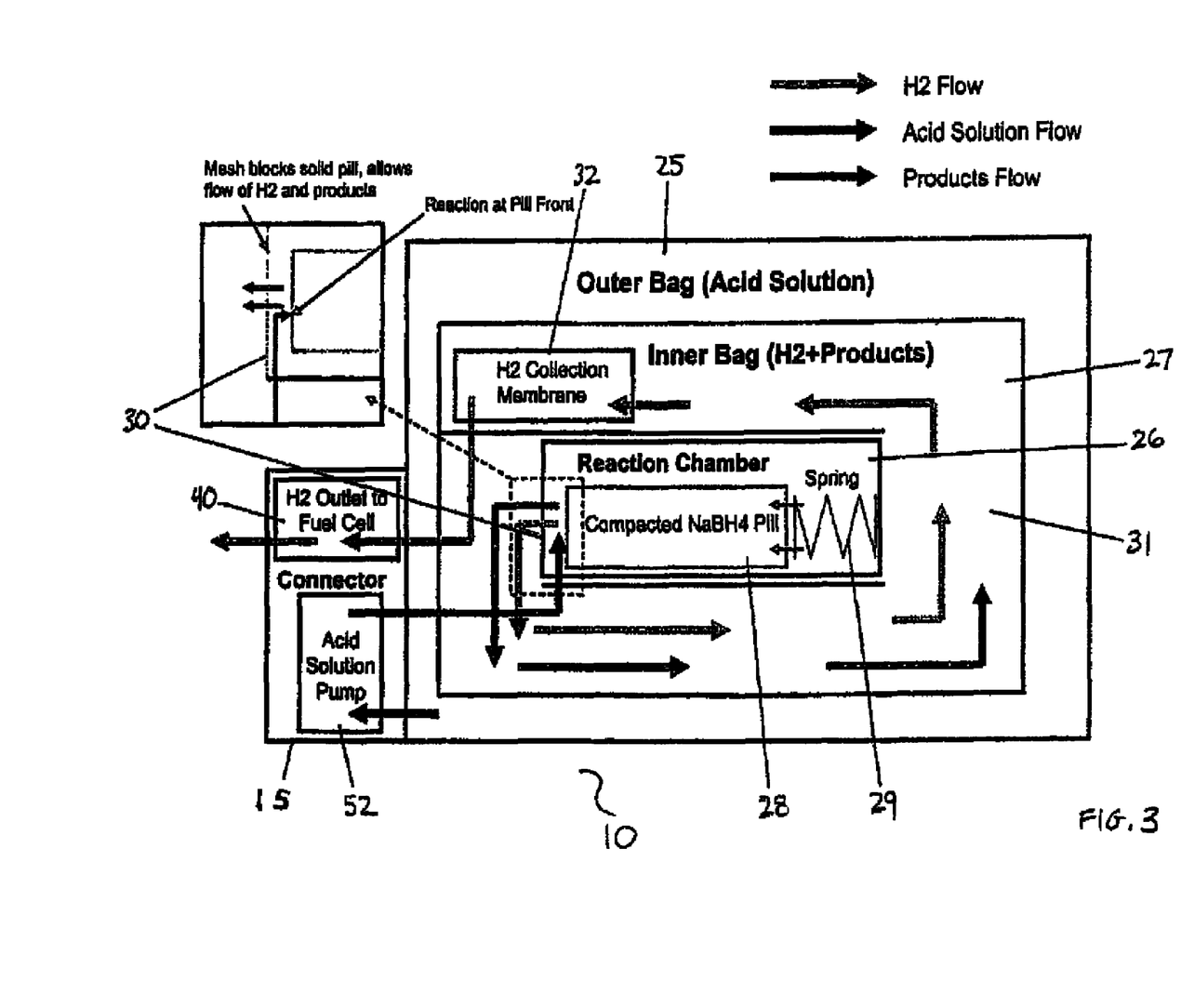
FIG. 3 is a schematic diagram of fluid flow inside the fuel cartridge.

The reaction chamber 26 should be constructed of a material that can both withstand the heat of the reaction, which can lead to temperatures in excess of 170° F. and will allow the pill 28 to slide under the force of the spring without binding. Teflon TEFLON® or polyethelyne both meet these requirements suitably.

The separator screen 30 has a mesh size that is smaller than the powder's grain size, thus preventing the pill 28 from exiting through the outlet, but allowing liquid, gas and particulates smaller than the screen openings to flow therethrough. Plastic mesh with a screen pitch of 0.080" and strand size of 0.005" is used in the current embodiment.

When the fuel cartridge 10 is coupled to the pump and connector sub-assembly 22 of the fuel cell system 12, acid solution can be pumped from the outer bag 25 through a pumping chamber 52 inside the connector sub-assembly 15 and into the reaction chamber 26 near the separator screen 30. When the acid solution and $NaBH_4$ mix, hydrogen gas and a waste slurry is formed; the pressure of the spring 29 forces the gas and slurry through the separator screen 30 and into a product collection portion of the inner bag 27 ("product collector" 31). The slurry comprises solids suspended in liquid, and in particular, is a mixture of sodium metaborate, water, and a salt of an acid, and has a benign acidity of around pH 7. The particular size of the slurry solids should be smaller than the mesh size of the separator screen 30 so that the slurry solids can pass there-through. At the downstream end of the product collector 31 is a hydrogen gas separation membrane 32, which is permeable to hydrogen gas but impermeable to liquid and solid. Hydrogen gas is separated from the slurry and delivered to fuel cell system 10 via an outlet port 40 in the connector sub-assembly 15.

Figure 4:
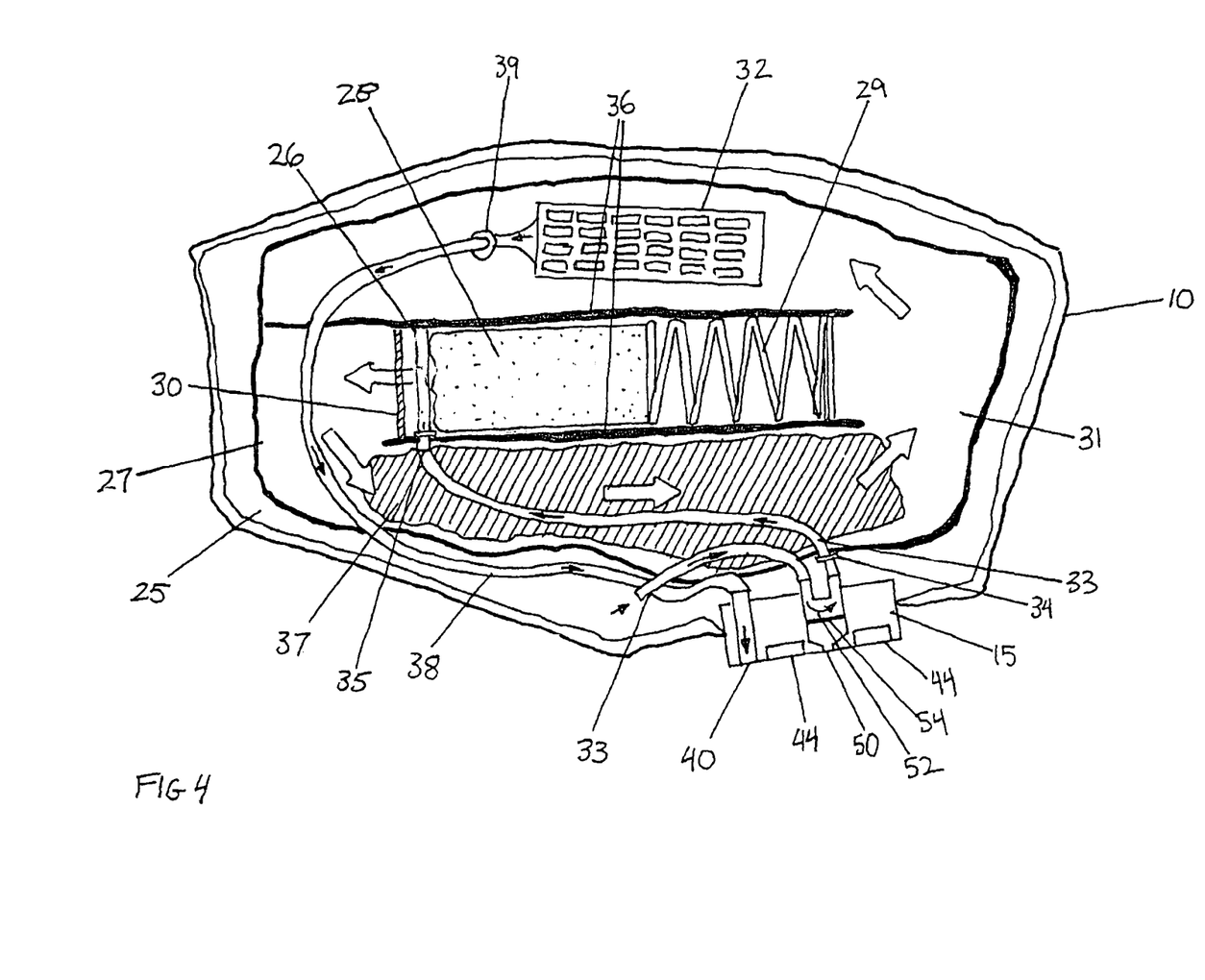
FIG. 4 is a partially transparent side view of the fuel cartridge.

FIG. 4 illustrates the construction of the fuel cartridge 10 in greater detail. The inner bag 27 is located inside the outer solution bag 25, such that the acid solution resides in the volume in between the solution bag 25 and inner bag 27. In the current embodiment, 6 mil urethane (Stevens Urethane, East Hampton, Mass., US) was heat welded to form the inner and outer bags 25, 27. A solution feed conduit 33 fluidly couples this volume to the pumping chamber 52, and also extends from the pumping chamber 52 through the inner bag at opening 34 and to a nozzle 35 in the reaction chamber 26 near the separator screen 30. The nozzle 35 is an elongated tube (stainless steel hypodermic tubing with the distal end crimped and sealed and an orifice perpendicular to the central axis of the tube and facing the central axis of the pill 28, McMaster) that spans the diameter of the reaction chamber 26. Solution is discharged through the hole and contacts the pill 28. The distance between the nozzle and the separator screen 30 allows for mixing of the reactants prior to leaving the reaction chamber 26. Several alternatives known in the art exist for ensuring proper mixing of the reactants and products in order to maximize the yield of the reaction and the energy density of the cartridge 10. For example, the cartridge 10 can use a single nozzle or a plurality of nozzles (not shown) to help ensure more even mixing of the reactants. These nozzles could be a circular or linear array with orifices designed to mist, spray, or provide droplets to the pill 28. A distance and preferably tortuous path between the nozzle and the screen 30 allows for thorough mixing of the reactants prior to leaving the reaction chamber 26. In the current embodiment, the nozzle 35 is 0.4" from the separator mesh, although the optimum distance will vary with the nozzle design, flow rates, etc. An additional feature that has been found to be advantageous in the reaction area design is to construct the nozzle 35 such that the reacting pill can form around the nozzle 35 as it is reacted by the solution from the nozzle 35. This ensures intimate contact between the nozzle 35 and the pill 28 and a reasonably tortuous path for the fluids before they exit the reaction chamber 26. An additional advantage of the current embodiment in which the reaction area is limited to the end of the pill is that the heat of reaction can be contained in a relatively small space, maximizing the temperature of the reaction area. This higher temperature has favourable effects on the reaction efficiency, kinetics, and the ability to restart the system 12 with reaction products collected and hardened about the separator screen 30.

As the spring 29 is applying continuous pressure on the pill 28 against the separator screen 30, product hydrogen gas and waste slurry are discharged through the separator screen 30 and into the product collector 31, which has a serpentine flow path formed by two generally straight welds 36 which join the inner bag surfaces together. The welds form a central pocket in which the cylindrical reaction chamber 26 is located. The product collector 31 is partially filed with a liquid absorbing material 37 for absorbing water and other liquid in the slurry. This material minimizes the contact of the slurry with the gas collection membrane, as the slurry tends to form an impermeable coating on the membrane after prolonged exposure. Although higher performance materials exist, the highly absorbent material found in tampons was found to perform suitably for this application. Unabsorbed slurry and hydrogen gas continue along the product collector 31 to the gas separation membrane 32. Hydrogen gas flows through the separation membrane 32 (VERSAPOR® 3000 (Pall, Ann Arbor, MI) and into a hydrogen delivery tube 38, which is coupled to the separation membrane 32 and extends through the inner bag at opening 39 and couples to the discharge port 40 in the connector sub-assembly 15. The flow path of the solution, waste slurry and hydrogen gas are illustrated by arrows in this figure.

While mixing water alone with the NaBH$_4$ is sufficient to chemically produce hydrogen gas, the reaction rate is slow. Preferably, the acid is provided to speed up the reaction rate; in this sense, the acid acts like a catalyst, although the acid is consumed in the reaction. While in this embodiment, 28 wt. % citric acid solution is reacted with NaBH$_4$ powder to generate hydrogen, any acid solution with a suitable pH can be substituted. Preferably, the acid solution has a pH of 6 or less; more preferably, the acid solution has a range of 2 or less. The 28 wt. % citric acid solution has a pH of about 2. This concentration was found to provide a desirable balance of low pH, fast rate of reaction, and minimal wastage of acid. That is, substantially all of the acid in the solution was consumed in the reaction. When selecting alternative acids, such a balance is also desirable.

Alternative liquid and solid reactants that produce hydrogen gas when mixed can be substituted. For example, tests have shown that the fuel cartridge 14 can mix aluminium with sodium hydroxide solution to produce hydrogen gas, in the following reaction:

$$2Al + 2NaOH + 6H_2O \rightarrow 2NaAl(OH)_4 + 3H_2 \qquad (1)$$

It is expected that other known reactions between reactants that produce hydrogen gas can be used in the fuel cartridge 10, provided that one of the reactants can be stored in compacted solid form, an another of the reactants can be separately stored in liquid form. The fuel cartridge 14 design is particularly effective for facilitating such reactions, as a portion of the solid is continuously exposed to the liquid reactant, since the biasing force provided by the spring 29 forces the gaseous, liquid and small particulate products of the reaction through the separator screen 30. This prevents the products of the reaction from coating the solid reactant, and from mixing with the liquid reactant. Care should be taken in selecting the solid powder grain size and separator screen size so that the solid reactant is not pushed through the separator screen 30.

While a spring 29 is used to provide a biasing force against the solid reactant, other biasing means can be provided. For example, the reaction chamber 26 can be a single-ended flexible sheath that is stretches when filled with the solid reactant, and applies pressure on the solid reactant towards the sheath's opening. Other equivalent biasing means can be readily substituted. In the embodiment shown in these Figures, and referring particularly to FIG. 1, the biasing spring 29 applies pressure against the pill 28 such that a portion of the pill 28 is always pressed against the separator screen 30. As the pill 28 is consumed, the spring 29 will expand; a clear window 41 is provided in the surface of the fuel cartridge 10 such that the amount of pill material is visible. This window 41 serves as a fuel gauge to display the amount of reactant left in the fuel cartridge 10.

Figure 5:
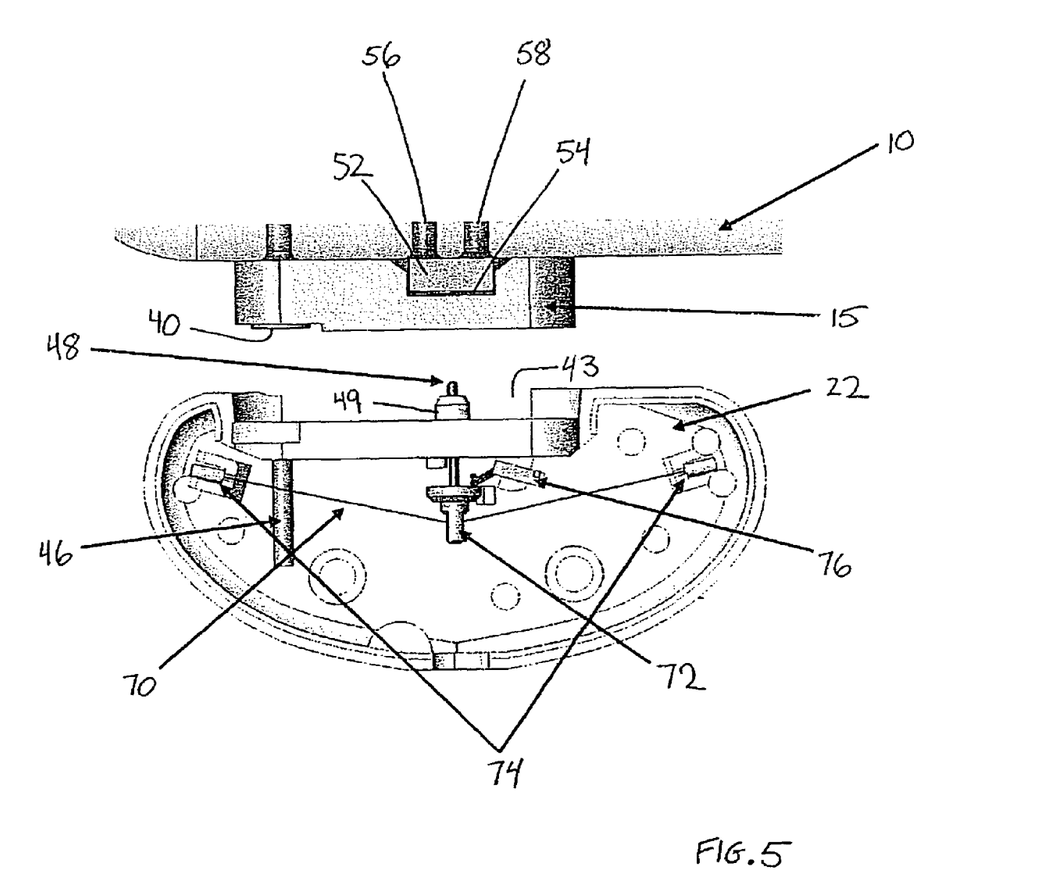
FIG. 5 is a schematic, partially transparent view of the connector and pump sub-assembly and the fuel cartridge connector sub-assembly.
Figure 6:
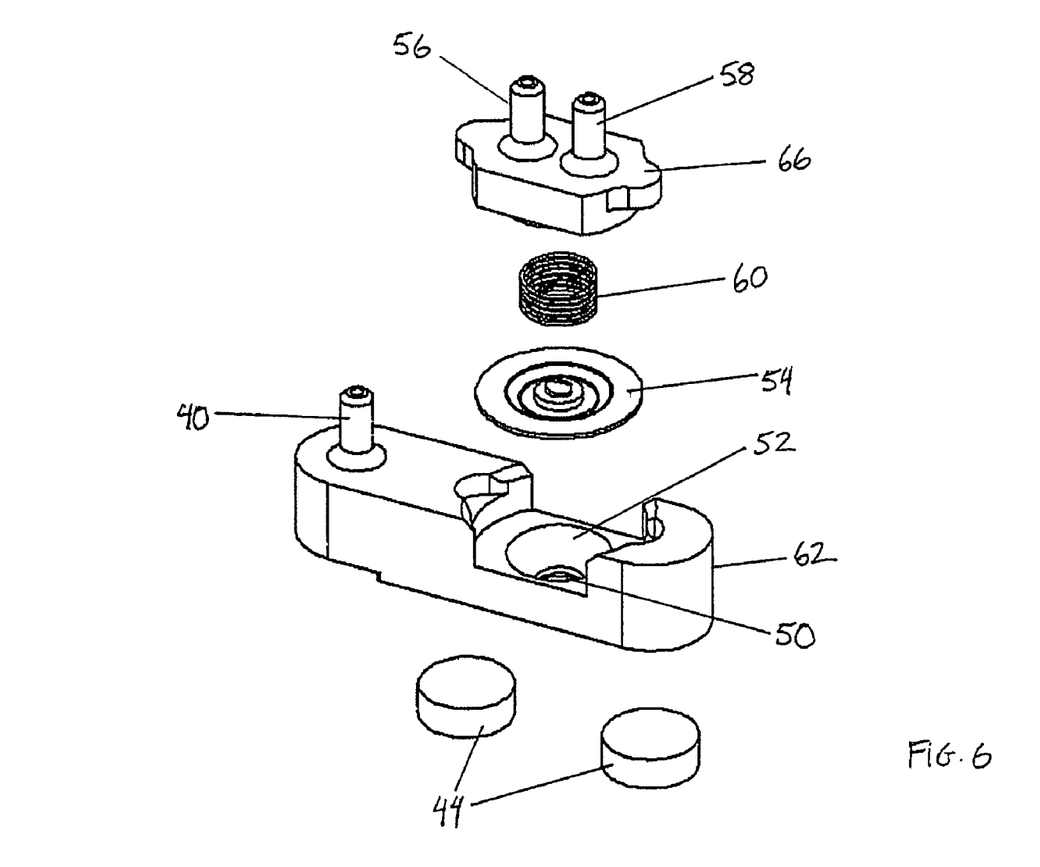
FIG. 6 is a schematic exploded perspective view of the fuel cartridge connector sub-assembly.

Referring now to FIGS. 5 and 6, the cartridge connector sub-assembly 15 protrudes from the fuel cartridge outer shell and can be connected to the pump and connector sub-assembly 22 of the fuel cell system 14. The pump and connector sub-assembly 22 has a recess 43 adapted to receive the protruding connector sub-assembly 15. A pair of magnets 44 are provided in the base of the connector sub-assembly 15, and are attracted to metal plates in the recess 43. The magnets 44 provide a means for securing the fuel cartridge 10 to the fuel cell system 12; however, other securing means as known in the art can be substituted within the scope of the invention.

The pump and connector sub-assembly 22 is provided with a hydrogen intake port 46 that mates with the hydrogen discharge port 40 when the fuel cartridge 10 is connected to the fuel cell system 12. A pump plunger 48 extends from the recess 43 of the pump and connector sub-assembly 22; a boss 49 protrudes from sub-assembly 22 around pump plunger 48, protecting the plunger 48 from damage when the connector sub-assembly 15 is not in place. A diaphragm port 50 is provided in the connector sub-assembly 15 that receives the pump plunger 48 when the fuel cartridge 10 and fuel cell system 12 are connected. The diaphragm port 50 extends into a bottom end of a pumping chamber 52. At a top end of the pumping chamber 52 are an acid solution inlet 56 and an acid solution outlet 58. A flexible diaphragm 54 is mounted inside the pumping chamber 52 and fluidly seals the pumping chamber volume from the diaphragm port 50; this confines the flow of acid solution from the inlet 56 into the pumping chamber 52nd out of the outlet 58. A biasing spring 60 is located in the second chamber portion and applies a biasing force against the diaphragm 54 to bias the diaphragm 54 in an unflexed position.

The acid solution inlet and outlet 56, 58 are fluidly coupled to the solution feed conduit 33.

The connector sub-assembly 22 has an outer shell comprising two molded plastic portions: an outer shell portion 62 contains a portion of the pumping chamber 52, the diaphragm port 50, hydrogen discharge port 40, and magnets 44. An inner shell portion 66 contains the rest of the pumping chamber 52, solution inlet 56 and outlet 58; the diaphragm 54 is fixed in place between the outer and central portions 62, 66. The shell portions 62, 66 are joined by LokTite 3105 Light Cure Adhesive. While the sub-assembly 22 is formed by joining together these shell portions by an adhesive, it is to be understood that many other methods known in the art are available for creating this sub-assembly 22.

When the fuel cartridge 10 and fuel cell system 12 are connected, a distal end of the pump plunger 48 extends through the diaphragm port 50, into the pumping chamber 52 and contacts the diaphragm 54. The pump plunger 48 is slidably constrained within the pumping and connector sub-assembly 22 in an axial direction and between a fully extended position -and a fully retracted position. When the pump plunger 48 is in its fully retracted position, it makes contact with but does not flex the diaphragm 54, i.e. the diaphragm 54 is in its unflexed position. When the pump plunger 48 is in its fully extended position, the diaphragm 54 is moved by the plunger 48 into its flexed position. The reciprocating movement of the pump plunger 48 causes the diaphragm 54 to oscillate, thereby creating a pumping pressure within the pumping chamber 52. This pumping pressure is effective to pump the citric acid solution from the solution bag 25 to the reaction chamber 26.

Recpriocating movement of the pump plunger 48 is achieved by contraction and extension of a shape memory alloy wire 70 connected to a plunger head 72 located at the proximal end of the pump plunger 48. The shape memory alloy wire 70 is comprised of a shape memory alloy material, such as a nickel-titanium alloy popularly known as "nitinol". The shape memory alloy material is sensitive to temperature or heat. For example, nitinol temporarily shrinks at a range of temperatures dictated by the composition of the nitinol; in this embodiment, the nintol wire 70 shrinks at about 100° C. The nitinol alloy will expand at a relative lower temperature and return to its original condition. In response to being heated above this shrinkage temperature, the nitinol alloy undergoes a dimensional change, such as a change in its length. In this way, the nitinol wire 70 can undergo a reduction in length and return to its original length repeatedly via repeated temperature cycling above its shrinkage temperature and cooling to below its expansion temperature.

It in the process of undergoing a dimensional change, as described above, the shape alloy material goes through a reversible phase transition or transformation, or a reversible structural phase transition, upon a change in temperature. Generally, such a transition represents a change in the material from one solid phase of the material to another, for example, by a change in the crystal structure of the material or by a re-ordering of the material at a molecular level. In the case of the nitinol wire 70, the superelastic alloy has a low temperature phase, or martensitic phase, and a high temperature phase, or austenitic phase. These phases can also be referred to in terms of a stiff phase and a soft and malleable phase, or responsive phase.

The nitinol wires 70 is threaded through the plunger head 72 and attached at either end to the pumping and connector sub-assembly 22 by crimp connections 74. The nitinol wire 70 is located such that when in its stiff phase, the plunger head 48 is in its retracted position; when the nitinol wire 70 is in its responsive phase, the plunger head 48 is in its fully extended position. The crimp connections 74 are connected to electrical wire (not shown) that is electrically coupled to a rechargeable battery (not shown) located in the control unit 23. The battery in turn is electrically connected to the electrical connectors 20 such that the battery can be recharged by electricity produced by the fuel cells 14. Electrical current through the nitinol wire 70 from the electrical wires will result in heating of the nitinol wire 70 above its shrinkage temperature, thereby causing the plunger 48 to move from its retracted position to its extended position, i.e. execute a compression stroke. When the plunger 48 reaches its fully extended position, the plunger head makes contact with a detector switch 76, which is electrically communicative with and sends a signal to the control unit 23. Upon receipt of this signal, the control unit 23 stops current flow from the battery or fuel cell system, and the wire 70 is allowed to cool and fall below its expansion temperature. Alternatively or additionally, the pulse length of the current provided to the wire 70 can be controlled by methods known in the art such that the wire is heated enough to cause it to contract. The wire 70 expands to its original length, and the plunger 48 is moved back into its fully retracted position, i.e. execute an expansion stroke. The frequency of the plunger strokes is dictated by the amount of hydrogen gas required; when more gas is required, more solution needs to be pumped to the reaction chamber 26, and the frequency of the plunger strokes is increased.

By locating certain pumping components, i.e. nitinol wire 70, plunger head 72, plunger 48 outside of the fuel cartridge 10, the manufacturing cost of the cartridge 10 is reduced. Also, by sealing the pumping chamber 52 with the diaphragm 52, the citric acid solution is not permitted to leave the fuel cartridge 10; this design minimizes the likelihood of damage or harm caused by acid leakage. The only fluid that is permitted to leave the fuel cartridge 10 is hydrogen gas, via port 40.

A further advantage offered by this design is the simplified control of gas generation. Since hydrogen gas is generated only when the citric acid solution is mixed with the solid NaBH$_4$, the rate of pumping entirely controls the rate of hydrogen gas production.

Although the present invention and its advantages have been described in detail, it should be understood that the present invention is not limited to or defined by what is shown or discussed herein. The drawings, descriptions and discussions herein show examples of the invention and provide examples of using the invention. One skilled in the art will realize the implementations of the present invention could be made without departing form the principles, spirit or legal scope of the present invention. Accordingly, the scope of the present invention should be determined by the following claims and their legal equivalents.

What is claimed is:

1. A fuel cell apparatus comprising:
   (a) a fuel cartridge comprising:
   a liquid reactant dispenser;
   a reaction chamber, separate from the liquid reactant dispenser, containing a solid reactant that produces hydrogen gas when mixed with a liquid reactant; and
   a connector sub-assembly comprising an inlet fluidly coupled to the liquid reactant dispenser, an outlet fluidly coupled to the reaction chamber, a flexible diaphragm in fluid communication with the inlet and outlet, and a hydrogen discharge port fluidly coupled to the reaction chamber; and
   (b) a fuel cell system removably coupled to the fuel cartridge, comprising:
   a fuel cell; and
   a connector sub-assembly, connectable to the fuel cartridge connector sub-assembly, comprising an actuator and a hydrogen intake port fluidly coupled to the fuel cell that aligns with the hydrogen discharge port when the fuel cartridge and fuel cell system are connected;
   wherein the actuator causes the diaphragm to reciprocate and pump a liquid reactant from the liquid reactant dispenser to the reaction chamber, wherein the liquid reactant is substantially contained within the fuel cartridge during the pumping, wherein the liquid reactant reacts within the reaction chamber to produce a fuel.

2. A fuel cell apparatus as claimed in claim 1 wherein the liquid reactant is citric acid solution and the solid reactant is sodium borohydride.

3. A fuel cell apparatus as claimed in claim 1 wherein the actuator is a shape memory alloy and is electrically coupled to an electrical source capable of heating the shape memory alloy to above a shrinkage temperature.

4. A fuel cell apparatus as claimed in claim 3 wherein the actuator is a nitinol wire coupled to a reciprocating member and attached at both ends to crimping connectors to form a bow-shaped configuration.

5. A fuel cell apparatus as claimed in claim 4 wherein the wire is mounted so that when in a stiff phase, the reciprocating member is in a retracted position, and when in a responsive phase, the reciprocating member is in an extended position.

6. A fuel cell apparatus as claimed in claim 1, wherein the diaphragm reciprocates between an unflexed state and a flexed state, wherein the inlet includes a first valve, and the outlet includes a second valve, wherein in the unflexed state, the inlet valve is substantially open and the outlet valve is substantially sealed, such that the liquid reactant flows through the inlet valve; and in the flexed state, the inlet valve is substantially sealed and the outlet valve is substantially open, such that the liquid reactant flows through the outlet valve.

7. A fuel cell apparatus as claimed in claim 1, wherein the fuel cartridge connector sub-assembly further includes a reciprocating member coupled to the actuator, wherein the actuator reciprocates the reciprocating member between two modes:
   a retracted mode wherein the reciprocating member does not transfer substantial force from the actuator to the diaphragm, wherein the diaphragm is in the unflexed mode; and
   an extended mode wherein the reciprocating member contacts the diaphragm to transfer a force from the actuator to the diaphragm, wherein the diaphragm is in the flexed mode.

8. A fuel cell apparatus as claimed in claim 7, wherein the reciprocating member contacts the diaphragm in the retracted mode.

9. A fuel cell apparatus as claimed in claim 8, wherein the reciprocating member is a pump plunger.

10. A fuel cell apparatus as claimed in claim 1, wherein the fuel cell apparatus further comprises a coupling mechanism that removably couples the fuel cell system to the fuel cartridge.

11. A fuel cell apparatus as claimed in claim 10, wherein the coupling mechanism is a magnetic coupler comprising a magnet and a metal plate magnetically attracted to the magnet, wherein the fuel cartridge connector sub-assembly further incorporates the magnet and the fuel cell system connector sub-assembly further incorporates the metal plate.

12. A fuel cell apparatus as claimed in claim 1 wherein the liquid reactant is water and the solid reactant is sodium borohydride.

* * * * *